US006821512B1

(12) United States Patent
Gao et al.

(10) Patent No.: US 6,821,512 B1
(45) Date of Patent: Nov. 23, 2004

(54) COMPOSITIONS AND METHODS FOR INCREASING PACKAGING AND YIELD OF RECOMBINANT ADENOVIRUSES USING MULTIPLE PACKAGING SIGNALS

(75) Inventors: Guangping Gao, Rosemont, PA (US); James M. Wilson, Gladwyne, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 161 days.

(21) Appl. No.: 10/169,544

(22) PCT Filed: Nov. 27, 2000

(86) PCT No.: PCT/US00/32235

§ 371 (c)(1),
(2), (4) Date: May 30, 2002

(87) PCT Pub. No.: WO01/40455

PCT Pub. Date: Jun. 7, 2001

Related U.S. Application Data

(60) Provisional application No. 60/169,025, filed on Dec. 3, 1999.

(51) Int. Cl.$^7$ .................. C12N 15/861; C12N 15/63; C12N 15/64; A61K 48/00
(52) U.S. Cl. ............... 424/93.2; 435/320.1; 435/455; 435/456; 435/457; 435/325; 435/69.1; 424/93.1; 424/93.6
(58) Field of Search ............. 435/320.1, 455, 435/456, 457, 325, 69.1; 424/93.1, 93.2, 93.6

(56) References Cited

U.S. PATENT DOCUMENTS 5,882,877 A * 3/1999 Gregory et al. .......... 435/320.1

FOREIGN PATENT DOCUMENTS

WO      WO99/53085 A2    10/1999

OTHER PUBLICATIONS

Kmiec, American Scientist, 1999, vol. 87, pp. 240–247.*
Verma et al., Nature, 1997, vol. 389, pp. 139–242.*
Fox, Nature Biotechnology, 2000, vol. 18, pp. 143–144.*
Anderson, Nature, 1998, vol. 392, pp. 25–30.*
Mountain, TIBTECH, 2000, vol. 18, pp. 119–128.*
Ross et al., Human Gene Therapy, 1996, vol. 7, pp. 1781–1790.*
P. Hearing et al, "Identification of a Repeated Sequence Element Required for Efficient Encapsidation of the Adenovirus Type 5 Chromosome", J. Virol., 61(8):2555–2558 (Aug., 1987).
M. Grable et al, "Adenovirus Type 5 Packaging Domain is Composed of a Repeated Element that is Functionally Redundant", J. Virol., 64(5):2047–2056 (May, 1990).
M. Grable et al, "cis and trans Requirements for the Selective Packaging of Adenovirus Type 5 DNA", J. Virol., 66(2):723–731 (Feb., 1992).
S. Kochanek et al, "A New Adenoviral Vector: Replacement of All Viral Coding Sequences with 28 kb of DNA Independently Expressing Both Full–Length Dystrophin and β–galactosidase", Proc. Natl. Acad Sci. USA, 93:5731–5736 (Jun., 1996).
M. Lanuti et al, "Evaluation of an $E_1E_1$–Deleted Adenovirus Expressing the Herpes Simplex Thymidine Kinase Suicide Gene in Cancer Gene Therapy", Human Gene Therapy, 10:463–475 (Feb., 1999).
K. Hehir et al, "Molecular Characterization of Replication–Competent Variants of Adenovirus Vectors and Genome Modifications to Prevent their Occurrence", J. Virol., 70(12):8459–8467 (Dec., 1996).
D. Von Seggern et al, "A Helper–Independent Adenovirus Vector with E1, E3, and Fiber Deleted: Structure and Infectivity of Fiberless Particles", J. Virol., 73(2):1601–1608 (Feb., 1999).
S. Schmid et al, "Bipartite Structure and Functional Independence of Adenovirus Type 5 Packaging Elements", J. Virol., 71(5):3375–3384 (May, 1997).
S. Schmid et al, "Cellular Components Interact with Adenovirus Type 5 Minimal DNA Packaging Domains", J. Virol., 72(8):6339–6347 (Aug., 1998).
V. Sandig et al, "Optimization of the Helper–Dependent Adenovirus System for Production and Potency in vivo", Proc. Natl. Acad. Sci., 97(3):1002–1007 (Feb., 2000).

* cited by examiner

*Primary Examiner*—David Guzo
(74) *Attorney, Agent, or Firm*—Howson and Howson

(57) ABSTRACT

A recombinant adenoviral vector which has multiple adenovirus packaging domains is provided. This vector has advantages over conventional adenoviral vectors in packaging plasmid vectors into adenoviral capsids. Methods of making and using this vector are described.

18 Claims, No Drawings

COMPOSITIONS AND METHODS FOR INCREASING PACKAGING AND YIELD OF RECOMBINANT ADENOVIRUSES USING MULTIPLE PACKAGING SIGNALS

CROSS-REFERENCE TO RELATED APPLICATIONS

This is a 371 of PCT/US00/32235, filed Nov. 27, 2000, which claims the benefit of the priority of U.S. patent application Ser. No. 60/169,025, filed Dec. 3, 1999.

This invention was made with financial assistance from the National Institutes of Health Grant No. P01 HD32649. The United States government has certain rights in this invention.

BACKGROUND OF THE INVENTION

The invention relates generally to the field of adenoviral vectors useful in delivering genes and methods of producing same.

Adenoviruses have been described as useful viral vectors for delivery of therapeutic genes into selected host cells. Due to interest in adenoviruses as delivery vehicles, several groups have investigated the mechanisms that allow selective packaging of the adenovirus (Ad) genome into viral capsids.

Within the left end of the Ad genome, a cis-acting packaging domain has been identified [M. Grable and P. Hearing, *J. Virol.* 64:2047–2056 (May 1990)]. Mutants of Ad serotype 5 (Ad5) lacking this region are nonviable but can be rescued by insertion of the left-terminal 355 nt at the right end of the viral genome. The Ad5 packaging domain has been found to function in an inverted orientation, and can be moved within several hundred base pairs from its original location without a reduction in virus yield [P. Hearing et al, *J. Virol.*, 61:2555–2558 (August 1987)].

The Ad5 packaging domain consists of at least seven elements which are functionally redundant. Four of the first five elements contain an AT-rich repeated sequence motif termed the A repeat. The fifth element does not contain any obvious primary sequence homology to the A repeat aside from the fact that it is also AT rich. With reference to the published sequences of Ad5, A repeat I is located within nt 240–248; A repeat II is located within nt 260–268; A repeat III is located within nt 302–311; A repeat IV is located within nt 313–321; A repeat V is located within nt 337–346; A repeat VI is located within nt 363 and 368 of Ad5; A repeat VII is located within nt 370–375 of Ad5 [M. Grable and P. Hearing, *J. Virol*, 66(2):723–731 (February 1992)]. The literature reports efforts to determine the minimum portion of the packaging domain required to package adenovirus DNA into virions. This approach is consistent with on-going efforts to maximize safety of the vectors, as well as to provide adequate space in the viral genome for heterologous gene sequences which are delivered by the adenoviral vectors.

The art continues to search for methods of optimizing production and yield of adenoviral vectors.

SUMMARY OF THE INVENTION

The present invention provides compositions and methods useful for efficiently packaging recombinant adenoviruses and producing high yields thereof. The invention involves engineering recombinant adenoviruses to contain multiple functional adenoviral packaging domains. Suitably, these vectors contain at least five of the "A" repeat elements of the adenoviral packaging domains, in duplicate. Most preferably, the vectors contain at least one intact adenoviral packaging domain and a second adenoviral packaging domain containing at least five "A" repeat elements.

Thus, in one aspect, the invention provides (a) an adenovirus 5' inverted terminal repeat, (b) a first adenovirus packaging domain, (c) a second adenovirus packaging domain; (d) a selected transgene under the control of regulatory sequences directing expression of the transgene, and (3) a 3' inverted terminal repeat. Suitably, the second packaging domain is located 5' to the native E1 region and the selected transgene.

In another aspect, the invention provides a pharmaceutical composition comprising a recombinant adenovirus of the invention and a physiologically compatible carrier.

In still another aspect, the invention provides a method of delivering a transgene to a selected host cell by infecting said cell with a recombinant adenovirus of the invention.

In a further aspect, the invention provides a method of increasing the packaging and yield of a selected recombinant adenovirus. The method involves engineering the selected recombinant adenovirus vector to contain at least two adenoviral packaging domains.

In yet a further aspect, the invention provides a method of producing a recombinant adenovirus which lacks functional adenoviral early, intermediate and late genes. The method involves co-culturing in a host cell (a) a recombinant adenoviral plasmid comprising multiple adenoviral packaging domains and a selected transgene, said plasmid lacking functional adenoviral early, intermediate and late genes; and (b) a helper virus. The rAd plasmids and helper virus, together with the host cell, provide sufficient adenoviral gene functions to permit packaging of the recombinant adenoviral plasmid into an adenoviral capsid.

Other aspects and advantages of the invention will be readily apparent from a review of the following detailed description of the invention.

DETAILED DESCRIPTION OF THE INVENTION

The present invention provides an adenoviral vector which comprises at least two adenoviral packaging domains, as defined herein. These vectors are characterized by enhanced packaging ability and yield, as compared to viral vectors containing native packaging signals. Thus, the invention provides compositions and methods which have significant advantages in the production of recombinant adenoviral vectors.

I. Recombinant Adenovirus Vectors

The recombinant adenoviral vectors of the invention are composed of, at a minimum, adenovirus 5' inverted terminal repeat sequences (ITRs), a first adenovirus packaging domain, a second adenovirus packaging domain, a selected transgene, and an adenovirus 3' ITR. As used herein, the term vector includes, without limitation, any genetic element, such as a plasmid, phage, transposon, cosmid, chromosome, virus, virion, etc.

The DNA sequences providing the adenoviral elements and encoding the adenovirus genes useful in this invention may be selected from among any known adenovirus type, including the presently identified 41 human types [see, e.g., Horwitz, cited above]. Similarly, adenoviruses known to infect other animals may supply the gene sequences. The selection of the adenovirus type for each adenoviral element or gene sequence does not limit this invention. The sequences for a number of adenovirus (Ad) serotypes, including that of Ad serotype 5, are available from the GenBank database. [See, e.g., GenBank, accession numbers NC-001406 (human Ad5, complete genome); NC-001460.1 (complete genome human Ad12); NC-001405 (complete genome human Ad2); AF0865670 (complete cds, human Ad15); AF086571.1 (complete cds, human Ad9); AF086570 (complete cds, human Ad8); AF086569 (complete cds, human Ad37); AF086568 (complete cds, human Ad19), among others]. A variety of adenovirus strains are available from the American Type Culture Collection, Manassas, Va., or are available by request from a variety of commercial and institutional sources. The adenovirus sequences used in the vectors of the invention may be derived from one or more wild-type adenoviruses or mutant adenoviruses.

A. Adenoviral ITRs

The 5' and 3' adenoviral inverted terminal repeats (ITRs) are located at the extreme 5' and extreme 3' ends of the adenoviral genome, respectively. The 5' and 3' ITRs are similarly located at or near the extreme termini of the recombinant adenoviral vectors of the invention. These ITRs may be obtained from any of the adenoviral serotypes described above, or may be artificial sequences, e.g., synthetic or mutated sequences that have the same or equivalent packaging functions as native ITRs.

B. Adenovirus Packaging Domain

As used herein, the term "adenovirus packaging domain" refers to the nucleic acid sequences of the adenoviral repeat elements required to package an adenoviral vector into a capsid protein. Although the packaging domain of the Ad5 is among the best studied of the human serotypes [see, Grable and Hearing (1992), cited above], this invention is not so limited. The repeat sequences of other adenoviral serotypes may be readily substituted in the present invention. Further, one of skill in the art may substitute functional fragments of one or more of the A repeat sequences. Additionally, the repeat elements and/or their functional fragments may be produced synthetically using conventional methods.

Further, in addition to the specific A repeats which have been identified, additional sequences may be included in the adenoviral packaging domains used in the vectors of the invention. For convenience, one may utilize an intact or partial native adenoviral packaging domain which, in addition to containing the A repeat elements, further comprises adenovirus E1a enhancer sequences. Thus, the adenovirus sequences of the packaging domain may extend 3' and/or 5' beyond the functional repeat elements. For example, one suitable adenovirus packaging domain may contain nt 218–354 of Ad5 which encompasses repeats I–V. In another example, a suitable adenovirus packaging domain may contain nt 186–371 which encompasses repeats I–VI and contains a partial repeat VII. Alternatively, the adenoviral packaging domains may further contain other sequences which serve to separate the individual repeat elements and/or the 5' ITRs from the repeats of the adenoviral packaging domain and/or which serve to separate the multiple adenoviral packaging domains. For example, where used to separate individual repeat elements, such sequences may be from 5 bp to 200 bp, 10 bp to 100 bp, 20 bp to 60 bp, or 30 bp to 50 bp in length. However, the length of these sequences may be readily adjusted as needed for convenience. These sequences may be viral in nature, or may obtained from other recombinant or synthetic means, and do not significantly impair the packaging function of the adenoviral packaging domain.

The adenoviral vectors of the invention contain multiple packaging domains (i.e., at least two packaging domains, and optionally three, four, five, six or more). Suitably, the adenoviral vectors contain a first adenoviral packaging domain which contains A repeat elements I through V and a second adenoviral packaging domain. Preferably, the second adenoviral packaging domain contains at least five A repeat elements, and most preferably, A repeat elements I through V. However, the second adenoviral packaging domain is not so limited and one of skill in the art may readily design the adenoviral vector such that the second adenoviral packaging domain contains as few as two, three or four of the A repeat element selected from I through VII). In one preferred embodiment, the first adenoviral packaging domain contains A repeat elements I through VII and the second adenoviral packaging domain contains at least A repeat elements I through V. For example, if such a vector is produced using Ad5 packaging domains, the vector contains two packaging domains of nt 240–346, together with the other vector elements. Alternatively, an adenoviral vector contains a first packaging domain of nt 240–375 (repeats I–VII) and a second packaging domain of nt 240–346 (repeats I–V), together with the other vector elements.

An adenoviral vector of the invention may contain multiple copies of selected repeat elements located directly after one another, but located within one complete adenoviral packaging domain. For example, an adenoviral vector of the invention may contain the sequences encompassing repeats I–V, a second packaging domain encompassing repeats I–V, followed by the sequences encompassing repeats VI and VII. As another example, an adenoviral vector of the invention may contain the sequences encompassing repeats I–VI, a second packaging domain encompassing repeats I–VI, following the sequences encompassing repeat VII. Alternatively, the adenoviral vector of the invention may contain the multiple packaging domains located in tandem. For example, an adenoviral vector of the invention may contain the sequences encompassing repeats I–VII followed by the sequences encompassing repeats I–V.

According to the present invention, both the first and second adenoviral packaging domains are located within 100 to 400 bp from the left terminus of the adenoviral vector and 5' to the E1 sequences, if the E1 sequences are intact. Thus, the first and second adenoviral packaging domains are preferably located within map units 0–1 of the adenoviral genome. Additionally, the first and second adenoviral packaging domains are located 5' to the transgene sequences. Preferably, at least one of the adenoviral packaging domains is located in its native location, i.e., 3' to the adenoviral 5' ITR sequences and no more than 375 bp from the left terminus of the adenoviral vector. In one preferred embodiment, the 5' ITRs and a first adenoviral packaging domain are both present in their native locations and the second adenoviral packaging domain is engineered to be no more than 20 to 200 bp 3' from the first adenoviral packaging domain. Optionally, the adenoviral packaging domains may be present in the constructs of the invention in either standard orientation or inverted orientation. Preferably, at least two of the multiple adenoviral packaging domains are in the same orientation.

The adenoviral vectors and viruses of the invention are useful for delivery of genes to host cells for a variety of purposes, which include both therapeutic and vaccinal uses. Because the adenoviral packaging domains are relatively small (i.e., in the range of about 100–190 bp) and recombinant adenoviral capsids can package vectors of up to 105% of the size of the native adenoviral genome (~36 kb), it is not necessary to delete any adenoviral genes to accommodate the second adenoviral packaging domain. Consequently, a second adenoviral packaging domain may be engineered 5' to the E1 region, even if the E1 genes are present in the vector.

C. Optional Adenoviral Elements

The present invention is not limited by the adenoviral genes which are present in the vector and may contain a minimal deletion (e.g., where only those adenoviral sequences are absent which are necessary for insertion of the sequences which encode the product to be expressed in the host cell) or may contain a functional deletion of one or all adenovirus genes. Thus, one of skill in the art may produce a recombinant adenoviral vector of the invention containing multiple adenoviral packaging domains, and other suitable adenoviral elements, as needed or desired.

As defined herein, "functional fragment" is that region of coding sequence or gene product which is required to provide the necessary or desired function. Such modifications may be deliberately introduced by resort to conventional genetic engineering or mutagenic techniques to enhance the function of the gene product(s) in some manner. Similarly included are any naturally occurring allelic variants or modifications of the nucleic acid sequence (e.g., a gene) or functional portion thereof. However, in addition to encompassing functional deletions of adenoviral sequences, the invention further encompasses deletions of adenoviral sequences which do not extinguish a desired gene function. For example, a suitable "non-functional" deletion may encompass a deletion of all of the E4 sequences except those sequences which encode the E4 ORF6 gene product.

For example, it is often desirable to render a recombinant adenovirus replication-defective for use in delivering genes to host cells. Thus, in one suitable embodiment, the adenoviral vector of the invention is rendered replication-defective by the absence of functional E1 genes (such a virus can not replicate in the absence of an external source of the necessary E1 gene products, E1a and E1b). Optionally, one may prepare a recombinant adenovirus of the invention containing functional deletions in one or more of the E1 genes (E1a, E1b), the E2 genes (E2a, E2b), E3, E4, intermediate genes IX, IXa, and late genes L1–L5.

An exemplary vector containing only the minimal adenoviral sequences is termed the ΔAd vector. This vector lacks all functional adenoviral genes including E1, E2, E3, E4, intermediate gene IX, IXa and late genes L1, L2, L2, L4 and L5. However, in a preferred embodiment, the adenoviral vector contains, in addition to the multiple packaging domains and minimal adenoviral sequences described above, functional adenoviral E2, E4, and IX genes. In another suitable embodiment, the adenoviral sequences in the adenoviral vector include the 5' and 3' cis-elements, the multiple packaging domains, functional E2 and E4 genes, intermediate genes IX and IXa, and late genes L1 through L5. However, the adenoviral vector may be readily engineered by one of skill in the art, taking into consideration the minimum sequences required, and is not limited to these exemplary embodiments. Suitably, where the adenoviral vector lacks all adenoviral functional genes, the IX sequences are supplied in trans by a helper virus. The transgene is operatively linked to regulatory components of the vector in a manner which permits transgene transcription.

D. Transgene

The transgene sequence is a nucleic acid sequence, heterologous to the Ad sequence, which encodes a polypeptide or protein of interest. The transgene is a nucleic acid sequence, heterologous to the adenovirus sequence, which encodes a polypeptide, protein, or other product, of interest. The composition of the transgene sequence depends upon the intended use for the resulting rAd of the invention. For example, one type of transgene sequence comprises a reporter or marker sequence which, upon expression, produces a detectable signal. Such reporter or marker sequences include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, membrane bound proteins including, for example, CD2, CD4, CD8, and the influenza hemagglutinin protein, as well as others well known in the art. Advantageously, high affinity antibodies to such proteins exist or can be made routinely, as can fusion proteins comprising a membrane bound protein appropriately fused to an antigen tag domain from, among others, hemagglutinin or Myc. These sequences, when associated with regulatory elements which drive their expression, provide signals detectable by conventional means. Such conventional means include enzymatic, radiographic, colorimetric, fluorescence or other spectrographic assays, fluorescent activated cell sorting assay and immunological assays, including ELISA, RIA and immunohistochemistry. For example, where the transgene is the LacZ gene, the presence of rAd is detected by assays for beta-galactosidase activity. Similarly, where the transgene is luciferase, rAd may be measured by light production in a luminometer.

However, desirably, the transgene is a non-marker gene which can be delivered to a cell or an animal via the rAd of the invention. The transgene may be selected from a wide variety of gene products useful in biology and medicine, such as proteins, antisense nucleic acids (e.g., RNAs), or catalytic RNAs. The rAd of the invention are useful for delivery of gene products which induce an immune response, e.g., for vaccine purposes. Suitable gene products may be readily selected by one of skill in the art from among immunogenic proteins and polypeptides derived from viruses, as well as from prokaryotic and eukaryotic organisms, including unicellular and multicellular parasites.

In another alternative, the rAd of the invention are useful for delivery of a transgene which encodes any product desirable for study. The selection of the transgene sequence is not a limitation of this invention. Choice of a transgene sequence is within the skill of the artisan in accordance with the teachings of this application.

In one particularly desirable embodiment, the rAd vectors of the invention are useful for correcting or ameliorating gene deficiencies, wherein normal genes are expressed but at less than normal levels. The rAd vectors may also be used to correct or ameliorate genetic defects wherein a functional gene product is not expressed. A preferred type of transgene sequence is a therapeutic gene which expresses a desired gene product in a host cell. These therapeutic nucleic acid sequences typically encode products which, upon expression, are able to correct or complement an inherited or non-inherited genetic defect, or treat an epigenetic disorder or disease.

Thus, the invention includes methods of producing a rAd vector which can be used to correct or ameliorate a gene defect caused by a multi-subunit protein. In certain situations, a different transgene may be used to encode each subunit of the protein. This is desirable when the size of the DNA encoding the protein subunit is large, e.g., for an immunoglobulin or the platelet-derived growth factor receptor. In order for the cell to produce the multi-subunit protein, a cell would be infected with rAd containing each of the different subunits. Alternatively, different subunits of a protein may be encoded by the same transgene. In this case, a single transgene would include the DNA encoding each of the subunits, with the DNA for each subunit separated by an internal ribosome entry site (IRES). This is desirable when the size of the DNA encoding each of the subunits is small, such that the total of the DNA encoding the subunits and the IRES is less than five kilobases.

Useful gene products include hormones and growth and differentiation factors including, without limitation, insulin, glucagon, growth hormone (OH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factors (CTGF), basic fibroblast growth factor (bFGF), acidic fibroblast growth factor (aFGF), epidermal growth factor (EGF), transforming growth factor a (TGFα), platelet-derived growth factor (PDGF), insulin-like growth factors I and II (IGF-I and IGF-II), any one of the transforming growth factor β (TGFβ) superfamily comprising TGFβ, activins, inhibins, or any of the bone morphogenic proteins (BMP) BMPs 1–15, any one of the heregulin/neuregulin/ARIA/neu differentiation factor (NDF) family of growth factors, nerve growth factor (NGF), brain-derived neurotrophic factor (BDNF), neurotrophins NT-3 and NT4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Other useful gene products include proteins that regulate the immune system including, without limitation, cytokines and lymphokines such as thrombopoietin (TPO), interleukins (IL) IL-1α, IL-1β, IL-2, IL-3, IL4, IL-5, IL-6, IL-7, IL-8, IL-9, IL-10, IL-11, IL-12, IL-13, IL-14, IL-15, IL-16, and IL-17, monocyte chemoattractant protein (MCP-1), leukemia inhibitory factor (LIF), granulocyte-macrophage colony stimulating factor (GM-CSF), Fas ligand, tumor necrosis factors α and β (TNFα and TNFβ), interferons (IFN) IFN-α, IFN-β and IFN-γ, stem cell factor, flk-2/flt3 ligand. Gene products produced by the immune system are also encompassed by this invention. These include, without limitations, immunoglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered MHC molecules including single chain MHC molecules. Useful gene products also include complement regulatory proteins such as membrane cofactor protein (MCP), decay accelerating factor (DAF), CR1, CR2 and CD59.

Still other useful gene products include any one of the receptors for the hormones, growth factors, cytokines, lymphokines, regulatory proteins and immune system proteins. The invention encompasses receptors for cholesterol regulation, including the LDL receptor, HDL receptor, VLDL receptor, and the scavenger receptor. The invention also encompasses gene products such as the steroid hormone receptor superfamily including glucocorticoid receptors and estrogen receptors, Vitamin D receptors and other nuclear receptors. In addition, useful gene products include transcription factors such as jun, fos, max, mad, serum response factor (SRF), AP-1, AP-2, myb, MRG1, CREM, Alx4, FREAC1, NF-xB, members of the leucine zipper family, C2H4 zinc finger proteins, including Zif268, EGR1, EGR2, C6 zinc finger proteins, including the glucocorticoid and estrogen receptors, POU domain proteins, exemplified by Pit1, homeodomain proteins, including HOX-1, basic helix-loop-helix proteins, including myc, MyoD and myogenin, ETS-box containing proteins, TFE3, E2F, ATF1, ATF2, ATF3, ATF4, ZF5, NFAT, CREB, HNF4, C/EBP, SP1, CCAAT-box binding proteins, interferon regulation factor 1 (IRF-1), Wilms tumor protein, ETS-binding protein, STAT, GATA-box binding proteins, e.g., GATA-3, and the forkhead family of winged helix proteins.

Other useful gene products include carbamoyl synthetase 1, ornithine transcarbamylase, arginosuccinate synthetase, arginosuccinate lyase, arginase, fumarylacetoacetate hydrolase, phenylalanine hydroxylase, alpha-1 antitrypsin, glucose-6-phosphatase, low-density-lipoprotein receptor, porphobilinogen deaminase, factor VIII, factor IX, cystathione beta-synthase, branched chain ketoacid decarboxylase, albumin, isovalcryl-CoA dehydrogenase, propionyl CoA carboxylase, methyl malonyl CoA mutase, glutaryl CoA dehydrogenase, insulin, beta-glucosidase, pyruvate carboxylase, hepatic phosphorylase, phosphorylase kinase, glycine decarboxylase (also referred to as P-protein), H-protein, T-protein, Menkes disease protein, tumor suppressors (e.g., p53), cystic fibrosis transmembrane regulator (CFTR), and the product of Wilson's disease gene PWD.

Other useful transgenes include non-naturally occurring polypeptides, such as chimeric or hybrid polypeptides or polypeptides having a non-naturally occurring amino acid sequence containing insertions, deletions or amino acid substitutions. For example, single-chain engineered immunoglobulins could be useful in certain immunocompromised patients. Other types of non-naturally occurring gene sequences include antisense molecules and catalytic nucleic acids, such as ribozymes, which could be used to reduce overexpression of a gene.

E. Other Vector Elements

Design of the transgene for expression in mammalian cells and hosts should include appropriate sequences that are operably linked to the gene of interest to promote its expression. "Operably linked" sequences include both expression control sequences that, are contiguous with the gene of interest and expression control sequences that act in trans or at a distance to control the gene of interest. Such expression control sequences are discussed in more detail in connection with the transgene.

Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. A great number of expression control sequences—native, constitutive, inducible and/or tissue-specific—are known in the art and may be utilized to drive expression of the transgene, depending upon the type of expression desired. For eukaryotic cells, expression control sequences typically include a promoter, an enhancer, such as one derived from an immunoglobulin gene, SV40, cytomegalovirus, etc., and a polyadenylation sequence which may include splice donor and acceptor sites. The polyadenylation sequence generally is inserted following the transgene sequences and before the 3' Ad ITR sequence. A rAd vector of the present invention may also contain an intron, desirably located between the promoter/enhancer sequence and the transgene. One possible intron sequence is also derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contains more than one polypeptide chains. Selection of these and other common vector elements are conventional and many such sequences are available [see, e.g., Sambrook et al, and references cited therein at, for example, pages 3.18–3.26 and 16.17–16.27 and Ausubel et al., *Current Protocols in Molecular Biology*, John Wiley & Sons, New York, 1989].

In one embodiment, high-level constitutive expression will be desired. Examples of such promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, *Cell*, 41:521–530 (1985)], the SV40 promoter, the dihydrofolate reductase promoter, the β-actin promoter, the phosphoglycerol kinase (PGK) promoter, and the EF1α promoter [Invitrogen]. Inducible promoters are regulated by exogenously supplied compounds, including, the zinc-inducible sheep metallothionine (MT) promoter, the dexamethasone (Dex)-inducible mouse mammary tumor virus (MMTV) promoter, the T7 polymerase promoter system [WO 98/10088]; the ecdysone insect promoter [No et al, *Proc. Natl. Acad. Sci. USA*, 23:3346–3351 (1996)], the tetracycline-repressible system [Gossen et al, *Proc. Natl. Acad. Sci. USA*, 82:5547–5551 (1992)], the tetracycline-inducible system [Gossen et al, *Science*, 20:1766–1769 (1995), see also Harvey et al, *Curr. Opin. Chem. Biol.*, 2:512–518 (1998)], the RU486-inducible system [Wang et al, *Nat. Biotech.*, 15:239–243 (1997) and Wang et al, *Gene Ther.*, 4:432–441 (1997)] and the rapamycin-inducible system [Magari et al, *J. Clin. Invest.*, 100:2865–2872 (1997)]. Other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

Another embodiment of the transgene includes a transgene operably linked to a tissue-specific promoter. For instance, if expression in skeletal muscle is desired, a promoter active in muscle should be used. These include the promoters from genes encoding skeletal α-actin, myosin light chain 2A, dystrophin, muscle creatine kinase, as well as synthetic muscle promoters with activities higher than naturally-occurring promoters [see Li et al., *Nat. Biotech.*, 17:241–245 (1999)]. Examples of promoters that are tissue-specific are known for liver [albumin, Miyatake et al. *J. Virol.*, 71:5124–32 (1997); hepatitis B virus core promoter, Sandig et al., *Gene Ther.*, 3:1002–9 (1996); alpha-fetoprotein (AFP), Arbuthnot et al., *Hum. Gene Ther.*, 7:1503–14 (1996)], bone [osteocalcin, Stein et al., *Mol. Biol. Rep.*, 24:185–96 (1997); bone sialoprotein, Chen et al., *J. Bone Miner. Res.*, 11:654–64 (1996)], lymphocytes [CD2, Hansal et al., *J. Immunol.*, 161:1063–8 (1998); immunoglobulin heavy chain; T cell receptor α chain], neuronal [neuron-specific enolase (NSE) promoter, Andersen et al. *Cell. Mol. Neurobiol.*, 13:503–15 (1993); neurofilament light-chain gene, Piccioli et al., *Proc. Natl. Acad. Sci. USA*, 8:5611–5 (1991); the neuron-specific vgf gene, Piccioli et al., *Neuron*, 15:373–84 (1995)]; among others.

Of course, not all vectors and expression control sequences will function equally well to express all of the transgenes of this invention. However, one of skill in the art may make a selection among these expression control sequences without departing from the scope of this invention. Suitable promoter/enhancer sequences may be selected by one of skill in the art using the guidance provided by this application. Such selection is a routine matter and is not a limitation of the molecule or construct. For instance, one may select one or more expression control sequences, operably link the sequence to a transgene of interest, and insert the "minigene" comprising the expression control sequence and the transgene into an Ad vector. After following one of the methods for packaging the rAd taught in this specification, or as taught in the art, one may infect suitable cells in vitro or in vivo. The number of copies of the transgene in the cell may be monitored by Southern blotting or quantitative PCR. The level of RNA expression may be monitored by Northern blotting or quantitative RT-PCR. The level of protein expression may be monitored by Western blotting, immunohistochemistry, ELISA, RIA, or tests of the transgene's gene product's biological activity. Thus, one may easily assay whether a particular expression control sequence is suitable for a specific transgene, and choose the expression control sequence most appropriate for expression of the desired transgene.

II. Production of Recombinant Adenoviral Vectors

Conventional techniques may be utilized for construction of the adenoviral vectors and other nucleic acid molecules of the invention. See, generally, Sambrook et al, Molecular Cloning: A Laboratory Manual, Cold Spring Harbor Laboratories, Cold Spring Harbor, N.Y. Once the desired adenoviral vector (e.g., a plasmid) is engineered, it may be transferred to a host cell for packaging into a viral capsid by any suitable method. Such methods include, for example, transfection, electroporation, liposome delivery, membrane fusion techniques, high velocity DNA-coated pellets, viral infection and protoplast fusion. Thereafter, cells are cultured according to standard methods.

The mammalian host cell itself may be selected from any mammalian species, such as human cell types, including, without limitation, cells such as CHO, BKH, MDCK, and various murine cells, e.g., 10T1/2 and WEHI cells, African green monkey cells such as VERO, COS1, COS7, BSC1, BSC 40, and BMT 10, and human cells such as W138, MRC5, A549, human embryonic retinoblast (HER), human embryonic kidney (HEK), human embryonic lung (HEL), and TH1080 cells. In a preferred embodiment, appropriate cells include 293 cells (human embryonic kidney cells which express adenoviral E1a and E1b proteins), 911, PER.C6 cells (human embryonic retinoblast cells that express adenoviral E1; see WO 97/19463), GH329 cells (a cell line that expresses adenoviral E1); 27–18 cells, 84–31 cells (293-based cells that express adenovirus E1a, E1b and E4 [G. Gao, *J. Virol.*, 70(12):8934–8943 (1996)], 10–3 cells (293-based cells that express adenovirus E1a, E1b and E4ORF6 [G. Gao, *J. Virol.*, (1996)], 3T3 cells (mouse embryonic fibroblast cell line), NIH3T3 cells (subline of 3T3 cells), HepG2 cells (human liver carcinoma cell line), Saos-2 cells (human osteogenic sarcomas cell line), HuH7 cells or HeLa cells (human carcinoma cell line). Neither the selection of the mammalian species providing the cells nor the type of mammalian cell is a limitation of this invention.

Suitably, where the selected recombinant vector contains a functional E1 deletion, the vector is introduced into and cultured in E1-complementing cells using conventional techniques, such as the transfection techniques known in the art [see, K. Kozarsky et al, *Som. Cell and Molec. Genet.*, 19(5):449–458 (1993)]. Thereafter, recombinant adenoviruses are isolated and purified following transfection. Where the selected recombinant vector contains functional deletions in adenovirus genes, these adenovirus genes (or functional fragments thereof) are supplied by a helper virus, a packaging cell, or a combination thereof. For example, if the recombinant vector construct of the invention contains a functional deletion in the E1 and E4 genes, the vector may be packaged into a viral capsid by culturing the cell in an E1/E4-complementing cell line (e.g., 84–31, 27–18, or 10–3 cells). Alternatively, the vector may be packaged by culturing the cell in an E1-complementing cell line in the presence of a helper virus which supplies the E4 function. Similarly, other recombinant vectors of the invention which contain a functional deletion in an adenoviral gene may be packaged in a selected host cell, optionally in the presence of a helper virus where the host cell does not supply all necessary adenovirus gene functions. The selection of the host cell and any necessary helper virus are well within the ability of one of ordinary skill in the art.

Although these host cells and helper viruses are known in the art, the constructs of the invention provide a significant advantage in such systems. Such advantages are perhaps most readily recognized where a helper virus is required for production. The separation of a desired packaged recombinant adenovirus from a culture also containing helper virus has long been a problem which has existed in the art. For example, if the recombinant vector of the invention contains functional deletions of all adenoviral genes, a helper virus is required to supply the adenoviral gene IX function and the function of any adenoviral genes not provided by the host cell. In one embodiment, the host cell line is an E1-complementing cell line (e.g., 293 cells) and the helper virus provides the E2, E3, E4, intermediate gene IXa and late genes L1–L5. The compositions of the present invention provide a significant advantage in production of such a deleted adenovirus over prior art methods. Particularly, the recombinant adenoviruses of the invention have an advantage in packaging and growth over other recombinant adenoviruses. Thus, the recombinant adenoviruses of the invention significantly outgrow the helper virus used in this production method.

The recombinant adenovirus vectors of the invention may be readily purified from culture using methods well known to those of skill in the art. The helper viruses may be removed from the culture using any of a variety of known systems including the Cre-Lox system [See, WO 98/10086], a restriction enzyme system [International Patent Application No. PCT/US00/00415, filed Jan. 7, 2000, for "Compositions and Methods Useful for Production of Recombinant Viruses Which Require Helper Viruses"]. The viruses may be subjected to plaque purification and the lysates subjected to cesium chloride centrifugation to obtain purified virus. The cells are subjected to two to three rounds of freeze-thawing. The resulting lysate is subjected to centrifugation for collection, and the supernatant is collected. Conventional purification techniques such as chloride gradient centrifugation or column chromatography are used to concentrate the rAd from the cellular proteins in the lysate.

III. Method of Delivering a Transgene to a Host Cell

The adenoviruses according to the present invention are suitable for a variety of uses in vitro, ex vivo and in vivo.

The recombinant adenovirus vectors of the invention may be used to deliver a selected transgene to a host cell by any suitable means. In one embodiment, the vectors and the cells are mixed in vitro and the infected cells are cultured using conventional methodologies.

Alternatively, the recombinant adenovirus vectors, preferably suspended in a physiologically compatible carrier, may be administered to a human or non-human mammalian patient. Suitable carriers may be readily selected by one of skill in the art in view of the indication to which the vector is directed, e.g., whether therapeutic or vaccinal. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present invention.

Optionally, the compositions of the invention may contain, in addition to the recombinant adenovirus vectors and carriers, other conventional pharmaceutical ingredients, such as preservatives, chemical stabilizers, or for vaccine use, adjuvants. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin. Suitable exemplary adjuvants include, among others, immune-stimulating complexes (ISCOMS), LPS analogs including 3-O-deacylated monophosphoryl lipid A (Ribi Immunochem Research, Inc.; Hamilton, Mont.), mineral oil and water, aluminum hydroxide, Amphigen, Avirdine, L121/squalene, muramyl peptides, and saponins, such as Quil A.

Any suitable route of administration may be used, including, direct delivery to the target organ, tissue or site, intranasal, intravenous, intramuscular, subcutaneous, intradermal and oral administration. Routes of administration may be combined within the course of repeated therapy or immunization.

In one embodiment, adenoviruses have been deemed suitable for applications in which transient transgene expression is therapeutic (e.g., p53 gene transfer in cancer and VEGF gene transfer in heart diseases). However, the adenoviruses are not limited to use where transient transgene expression is desired. The adenoviruses are useful for a variety of situations in which delivery and expression of a selected transgene is desired.

Suitable doses of E1-deleted adenoviruses may be readily determined by one of skill in the art, depending upon the condition being treated, the health, age and weight of the veterinary or human patient, and other related factors. However, generally, a suitable dose may be in the range of $10^{10}$ to $10^{18}$, and preferably about $10^{13}$ to $10^{16}$ viral particles per dose, for an adult human having weight of about 80 kg. This dose may be suspended in about 0.01 mL to about 1 mL of a physiologically compatible carrier and delivered by any suitable means. The dose may be repeated, as needed or desired, daily, weekly, monthly, or at other selected intervals.

Thus, the recombinant adenovirus vectors of the invention, which contain multiple adenoviral packaging domains, are useful for any of the variety of gene delivery applications known in the art for conventional adenoviral vectors. However, these recombinant adenoviruses of the invention provide significant advantages in that the constructs of the invention have improved packaging and generate higher yields of the recombinant adenoviruses, as compared to conventional adenoviral vectors.

The following examples are provided to illustrate production of the recombinant adenoviral vectors of the invention and uses therefor. These examples do not limit the scope of the invention. One skilled in the art will appreciate that, although specific constructs, reagents and conditions are outlined in the following examples, modifications can be made which are meant to be encompassed by the spirit and scope of the invention.

EXAMPLE 1

Production of Cloning Vector for Recombinant E1-Deleted Adenovirus with Multiple Packaging Sites Recombinant adenoviruses are created in E1-complementing cells through homologous recombination between a plasmid shuttle vector and an Ad5 viral backbone with a deletion in the E1 region.

To generate the duplicate adenovirus packaging domains, conventional polymerase chain reaction techniques can be used, followed by confirmation by sequencing that the insert is correct. Alternatively, duplicate adenovirus packaging domains may be generated using molecular cloning techniques.

The following examples create a cloning vector from viral isolates of H5.001CBhOTC which have either (a) Ad 5' ITRs, native Ad packaging/enhancer sequences (nt 218–354) which include repeat elements I–V, a repeat of Ad5 sequences 218–354, and the remaining native Ad packaging/enhancer sequences which include intact repeat elements VI and VII, or (b) Ad 5' ITRs, native Ad5 packaging/enhancer sequences (nt 186–371) which include repeat elements I–VI+, a repeat of Ad5 sequences 186–371, and the remaining native Ad packaging/enhancer sequences which includes an intact repeat element VII.

A. Recombinant Ad Cloning Vector with Repeat Elements I–V As Second Packaging Domain An adenoviral isolate was obtained which contains the 5' ITRs and a duplication of native Ad5 packaging domain elements I–V as described above. A fragment containing the ITRs and duplicate packaging domains was obtained from the adenoviral isolate as an approximately 1 kb fragment after BamHI digestion and the fragment was cloned into pBluescript at an EcoRV—BamHI site. Subsequently, the region corresponding to Ad5 map units (m.u.) 0–1 (including the duplicate Ad packaging domains) was removed from this new clone in a PstI-HincII digestion, and the clone was filled-in with polymerase. To create the modified pAdLink [Gil Hong Parl et al, *Korean J. Biochem.*, 21:91–97 (1995)] for cloning Ad vectors with multiple packaging domains, pAdLink (which contains native Ad5 mu 0–1, a polycloning site, and Ad5 m.u. 9–16) was digested with NheI and EcoRV to remove native Ad5 m.u. 0–1, and filled-in with polymerase. Subsequently, the clone containing Ad5 m.u. 0–1 with the duplicate packaging domains was inserted into the NheI and EcoRV sites to create the modified pAdLink. This modified pAdLink(I–V) now contains:

(a) Ad5 m.u. 0–1, which include Ad 5' ITRs, native Ad packaging/enhancer sequences (nt 218–354) which include repeat elements I–V, a repeat of Ad5 sequences (nt 218–354), and the remaining native Ad packaging/enhancer sequences which include intact repeat elements VI and VII;

(b) a polycloning site; and (c) Ad5 m.u. 9–16. The deletion of the Ad5 m.u. between 1 and 9 corresponds to a deletion in the E1 region.

In order to produce a recombinant Ad vector, a minicassette containing the desired promoter, transgene sequences, and a polyA site was subcloned into the polycloning site of the modified pAdLink(I–V) vector.

B. Recombinant Ad Cloning Vector with Repeat Elements I–VII as Second Packaging Domain A modified pAdLink was constructed essentially as described in Part A above, with the exception that the Ad5 map units 0–1 obtained from the viral isolate H5.001CBhOTC contain a duplication of native Ad5 packaging domain elements I–VI+ as described above. The modified pAdLink(I–VI+) now contains:

(a) Ad5 m.u. 0–1, which includes Ad 5' ITRs, native Ad5 packaging/enhancer sequences (nt 186–371) which include repeat elements I–VI+, a repeat of Ad5 sequences (nt 186–371) and the remaining native Ad packaging/enhancer sequences which include an intact repeat element VII;

(b) a polycloning site; and (c) Ad5 m.u. 9–16. The deletion of the Ad5 m.u. between 1 and 9 corresponds to a deletion in the E1 region.

In order to produce a recombinant Ad vector, a minicassette containing the desired promoter, transgene sequences, and a polyA site was subcloned into the polycloning site of the modified pAdLink(I–VI) vector.

EXAMPLE 2

Production of Recombinant E1-Deleted Adenoviruses with Multiple Packaging Domains A. Recombinant Ad with Duplicate Adenoviral Packaging Domain Elements I–V The plasmid shuttle vector is derived from the modified pAdLink(I–V) described above. A SalI site was introduced into a plasmid, pCMVβ [Clontech, Palo Alto, Calif.] using known techniques that allow the isolation of the fragment of this plasmid which includes a minigene containing the CMV promoter/enhancer, the LacZ gene, and polyA site, which minigene is already bordered at one end by a SalI site. Thereafter, the minigene was obtained from the modified pCMVβ plasmid by SalI digestion, and cloned into the pAdLink(I–V) to create a plasmid shuttle vector useful for production of a recombinant adenovirus. The plasmid shuttle vector contains from 5' to 3':

(a) Ad5 m.u. 0–1, which include the Ad 5' ITRs, native Ad packaging/enhancer sequences (nt 218–354) which include repeat elements I–V, a repeat of Ad5 sequences (nt 218–354), and the remaining native Ad packaging/enhancer sequences which include intact repeat elements VI and VII;

(b) a reporter minigene, which contains a CMV promoter/enhancer which controls expression of the LacZ transgene, and a polyA sequence; and (c) Ad5 m.u. 9–16. The deletion of the Ad5 m.u. between 1 and 9 corresponds to a deletion in the E1 region.

This plasmid shuttle vector is transfected into 293 cells (which express adenovirus proteins E1a and E1b) using conventional calcium phosphate techniques [B. Cullen, *Meth. Enzymol.*, 152:684–704 (1987)], together with the ClaI-restricted Ad5 backbone [ATCC], and cultured under standard conditions. Through homologous recombination, the vector is packaged into an Ad5 capsid to produce a recombinant adenovirus which contains elements (a) through (c) from the shuttle vector with a deletion in the E1 region.

The recombinant E1-deleted adenovirus is obtained from cell pellet prepared using conventional techniques, e.g., sonication and freeze-thaw techniques, optionally followed by purification by cesium-chloride step gradient. Because of the advantage provided by the presence of multiple packaging domains, significantly higher yields of the recombinant adenovirus of the invention, as compared to the virus providing Ad5 backbone, are obtained.

B. Recombinant Ad with Duplicate Repeat Elements I–VII

Another recombinant adenovirus was constructed using a similar procedure, except that the pCMVLink(I–VI+) plasmid was used. The resulting recombinant adenovirus contains, from 5' to 3':

(a) Ad5 m.u. 0–1, which includes Ad 5' ITRs, native Ad5 packaging/enhancer sequences (nt 186–371) which include repeat elements I–VI+, a repeat of Ad5 sequences (nt 186–371) and the remaining native Ad packaging/enhancer sequences which include an intact repeat element VII;

(b) a reporter minigene, which contains a CMV promoter/enhancer which controls expression of the LacZ transgene, and a polyA sequence; and (c) Ad5 m.u. 9–16, which are packaged into an Ad5 capsid.

EXAMPLE 3

Production of Recombinant E1/E4-Deleted Adenoviruses with Multiple Packaging Sites A recombinant adenovirus is created in an E1/E4-complementing cell through homologous recombination between a plasmid shuttle vector and a ClaI-restricted Ad5 mutant viral backbone with a 1.9 kb deletion in the E4 region, dl1004 [Bridge and G. Katner, *J. Virol.*, 63:6031–6038 (1989)]. The plasmid shuttle vector with duplicate repeat elements I–V contains from 5' to 3':

(a) Ad5 m.u. 0–1, which include the Ad 5' ITRs, native Ad packaging/enhancer sequences (nt 218–354) which include repeat elements I–V, a repeat of Ad5 sequences (nt 218–354), and the remaining native Ad packaging/enhancer sequences which include intact repeat elements VI and VII;

(b) a minigene, which contains human omithine transcarbamylase (OTC) expressed under the control of a CMV enhancer and chicken beta-actin promoter sequences, and a polyA sequence; and (c) Ad5 m.u. 9–16.

The plasmid shuttle vector is introduced into 84-31 cells (which express E1a, E1b and E4 protein) by calcium phosphate techniques, together with the dl1004, and the cells are cultured under standard conditions. Through homologous recombination, the plasmid shuttle vector is packaged into an Ad5 capsid to produce a recombinant adenovirus which contains elements (a) through (c) from the shuttle vector, with a deletion in the E1 region (Δ m.u. 1–9) and E4 region (Δ m.u. ~91.9–97.1).

A preliminary study, data not shown, has indicated that there are packaging and growth advantages in recombinant adenoviruses having duplicated packaging signals. This early study showed that through duplication of virus packaging sequences, E1/E4-deleted adenoviral vectors (with duplicate adenovirus packaging domains) could replicate in the E1/E4 complementing cell lines to levels that are similar to the level of an E1-deleted vector. These E1/E4-deleted vectors with multiple packaging domains thus have a 2–3 fold increase in vector yield over prior art constructs. Similar results are anticipated with the above-described composition.

EXAMPLE 4

Production of Recombinant E3-Deleted Adenoviruses with Multiple Packaging Sites

A recombinant adenovirus is created in an E1-complementing cell through homologous recombination between two plasmid shuttle vectors.

A first plasmid shuttle vector contains adenovirus sequences corresponding to adenovirus map units 0–16, which include the native 5' ITRs and the native Ad5 packaging/enhancer domain, and a second packaging domain which spans nt 240–346 of Ad [containing repeat elements I–V]. These sequences were cloned into a plasmid containing an intact E1 region as a PCR fragment obtained from amplification of the native Ad5 repeat elements I–V.

A second plasmid shuttle vector contains the remaining required adenovirus sequences to permit packaging, with the exception of the E1 region (m.u. 1–9) which function is provided by the packaging cells. This second plasmid shuttle vector therefore contains a minigene (which includes Ad m.u. 9–78.3, a reporter gene, LacZ, expressed under the control of CMV promoter/enhancer sequences, and a polyA sequence) inserted into the site of the E3-deletion (m.u. 78.3–m.u. 85.8), and Ad5 m.u.85.8–100.

The two plasmid shuttle vectors are transfected into 293 cells (which express E1a and E1b protein) and cultured under standard conditions. Through homologous recombination, a recombinant adenovirus which contains Ad5 m.u. 0–36, including the duplicate Ad packaging domains and a reporter minigene located in the site of the deletion in the E3 region (Δ m.u. 78.3–85.8) is obtained. The E1-intact adenovirus is obtained from culture using conventional freeze-thaw techniques and subjected to purification by cesium-chloride gradient.

Optionally, recombinant adenoviruses of the invention may be produced using other dual shuttle plasmid vector systems. In one such system, a first plasmid shuttle vector contains 5' ITRs, multiple packaging domains, and substantially all of the adenoviral gene, with the exception of the 3' ITRs. The second plasmid shuttle vector provides an intact 3' ITR and sufficient adenoviral sequences to permit efficient homologous recombination, and lacks 5' ITRs, the packaging/enhancer region, and an intact E1 region. This and other two-plasmid systems as may be readily designed by one of still in the art are useful for producing a recombinant adenovirus according to the invention using the methods described herein, and those which are well known to those of skill in the art.

All publications cited in this specification are incorporated herein by reference. While the invention has been described with reference to a particularly preferred embodiment, it will be appreciated that modifications can be made without departing from the spirit of the invention. Such modifications are intended to fall within the scope of the appended claims.

What is claimed is:

1. A recombinant adenoviral vector comprising (a) adenovirus 5' inverted terminal repeat sequences (ITRs), (b) a first adenovirus packaging domain, (c) a second adenovirus packaging domain; (d) a selected transgene under the control of regulatory sequences directing expression of the transgene, and (e) adenovirus 3' ITRs, wherein said packaging domains are located immediately 3' to the 5' ITRs.

2. The adenoviral vector according to claim 1, wherein said vector is a plasmid.

3. The adenoviral vector according to claim 1, wherein said vector is a virus.

4. The recombinant adenoviral vector according to claim 1, wherein the recombinant vector comprises two copies of the adenovirus region spanning repeats I–V of the adenoviral packaging domain.

5. The recombinant adenoviral vector according to claim 1, wherein the recombinant adenoviral vector comprises two copies of the adenovirus region spanning base pairs 218–354 of Ad5.

6. The recombinant adenoviral vector according to claim 1, wherein the recombinant adenoviral vector comprises two copies of the adenovirus region spanning base pairs 186–371 of Ad5.

7. The recombinant adenoviral vector according to claim 1, wherein the recombinant adenoviral vector comprises a functional deletion in one or more of the adenovirus early genes E1a, E1b, E2a, E2b, E3, E4, intermediate gene IX, intermediate gene IXa, and late genes L1, L2, L3, L4 and L5.

8. The recombinant adenoviral vector according to claim 1, wherein the recombinant adenoviral vector comprises a deletion in the native adenovirus E1 region.

9. A method of increasing the packaging and yield of a selected recombinant adenovirus, said method comprising the step of providing a host cell with a recombinant adenoviral vector according to claim 1, and culturing said host cell under conditions which permit packaging of said vector into a viral capsid.

10. The recombinant adenoviral vector according to claim 8, wherein the recombinant adenoviral vector further comprises a functional deletion in the E4 region.

11. The recombinant adenoviral vector according to claim 8, wherein the recombinant adenoviral vector comprises a mutation in a gene selected from E1a, E1b, E2a, E2b, E3 and E4.

12. A recombinant adenoviral vector comprising multiple adenovirus packaging signals, wherein the recombinant adenoviral vector comprises:

(a) adenoviral sequences consisting essentially of (i) adenovirus 5' inverted terminal repeat sequences (ITRs), (ii) a first adenovirus packaging domain comprising A repeats I–V, (iii) a second adenovirus packaging domain comprising A repeats I–V; (iv) 3' adenovirus ITRs; and functional deletions in each of the adenoviral genes E1, E2, E3, E4, intermediate gene IX, intermediate gene IXa, and late genes L1, L2, L3 and L5; and (b) a selected transgene under the control of regulatory sequences directing expression of the transgene.

13. A pharmaceutical composition comprising a recombinant adenoviral vector according to claim 12 and a physiologically compatible carrier.

14. A method of producing a recombinant adenovirus which lacks functional adenoviral early, intermediate and late genes said method comprising the step of co-culturing in a selected host cell:

(a) a recombinant adenoviral plasmid comprising two adenoviral packaging domain and a selected transgene, said plasmid lacking functional adenoviral early, intermediate and late genes; and (b) a helper virus, which together with the host cell, provides sufficient adenoviral gene functions to permit packaging of said recombinant adenoviral plasmid into an adenoviral capsid, wherein at least one of said two adenoviral packaging domains comprises at least one intact native adenoviral packaging domain consisting of A repeat elements I–VII.

15. The method according to claim 14, wherein at least one of said two adenoviral packaging domains comprises A repeat elements I–V of an adenoviral sequence.

16. The method according to claim 14, when the recombinant adenoviral vector comprises two copies of the adenovirus region spanning base pairs 186–371 of Ad5.

17. The method according to claim 14, wherein the recombinant adenoviral vector comprises two copies of the adenovirus region spanning base pairs 218–354 of Ad5.

18. A pharmaceutical composition comprising:

(a) a recombinant adenovirus adenoviral vector comprising (a) adenovirus 5' inverted terminal repeat sequences (ITRs), (b) a first adenovirus packaging domain, (c) a second adenovirus packaging domain; (d) a selected transgene under the control of regulatory sequences directing expression of the transgene, and (c) adenovirus 3' ITRs wherein said packaging domains are located immediately 3' to the 5' ITRs; and (b) a physiologically compatible carrier.

* * * * *